US009827131B2

United States Patent
Watts (10) Patent No.: US 9,827,131 B2
(45) Date of Patent: Nov. 28, 2017

(54) ANKLE-FOOT ORTHOSIS (71) Applicant: DORSET ORTHOPAEDIC COMPANY LIMITED, Hampshire (GB)

(72) Inventor: Robert John Watts, Hampshire (GB)

(73) Assignee: DORSET ORTHOPAEDIC COMPANY LIMITED, Hampshire (GB)

( * ) Notice: Subject to any disclaimer, the term of this patent is extended or adjusted under 35 U.S.C. 154(b) by 0 days.

(21) Appl. No.: 13/923,594

(22) Filed: Jun. 21, 2013

(65) Prior Publication Data

US 2013/0289463 A1    Oct. 31, 2013

Related U.S. Application Data (66) Continuation of application No. 11/792,473, Substitute for application No. PCT/GB2005/004685, filed on Dec. 6, 2005, now abandoned.

(30) Foreign Application Priority Data

Dec. 6, 2004 (GB) .................................. 0426729.0

(51) Int. Cl.
*A61F 5/01* (2006.01)
(52) U.S. Cl.
CPC .................................. *A61F 5/0111* (2013.01)
(58) Field of Classification Search
CPC ............................. A61F 5/0111; A61F 5/0113
(Continued)

(56) References Cited

U.S. PATENT DOCUMENTS 4,280,488 A    7/1981  Polsky et al.
4,554,912 A *  11/1985 Haberman ............ A61F 5/0111
                                                 206/390
(Continued)

FOREIGN PATENT DOCUMENTS

EP    1138288 A1    10/2001
EP    1848385 B1    4/2011
(Continued)

OTHER PUBLICATIONS

International Search Report for Application No. PCT/GB2005/004685 date of completion of search report Feb. 8, 2006.
(Continued)

*Primary Examiner* — Kari Rodriquez
(74) *Attorney, Agent, or Firm* — Holland & Hart (57) ABSTRACT

A preferred embodiment of the invention provides an ankle-foot orthosis (1) for resisting plantarflexion of a patient's foot, comprising a resiliently flexible sock-like orthotic structure (1) formed of first (12) and second (14) tubular sections set at an angle to one another, wherein the second tubular section is capable of being opened for insertion of the patient's foot and lower leg into respective ones of said first and second tubular sections, the orthosis further comprising at least one closure member (34) that can be passed round at least part of the periphery of the second tubular section and secured in place to urge the second tubular section towards a closed position in which the second tubular section is closely fitted to the lower leg of the patient.

20 Claims, 8 Drawing Sheets (58) Field of Classification Search
USPC .......... 602/27–29, 63, 65; 128/882, 892–894
See application file for complete search history.

(56) References Cited

U.S. PATENT DOCUMENTS

| | | | |
|---|---|---|---|
| 4,729,370 A | | 3/1988 | Kallassy |
| 4,862,900 A | | 9/1989 | Hefele |
| 4,865,023 A | * | 9/1989 | Craythorne ........... A61F 5/0111 602/27 |
| 5,094,232 A | | 3/1992 | Harris et al. |
| 5,176,624 A | * | 1/1993 | Kuehnreich ............. A43B 3/26 2/22 |
| 5,503,622 A | * | 4/1996 | Wehr .................... A61F 5/0127 128/882 |
| 5,827,211 A | * | 10/1998 | Sellinger ............... A61F 5/0195 602/10 |
| 5,833,640 A | | 11/1998 | Vazquez, Jr. |
| 5,853,380 A | | 12/1998 | Miller |
| 5,853,381 A | * | 12/1998 | Stevenson ............ A61F 5/0111 602/27 |
| 5,897,520 A | | 4/1999 | Gerig |
| 6,394,971 B1 | | 5/2002 | Slautterback et al. |
| 6,617,485 B2 | | 9/2003 | Herzberg |
| 6,908,445 B2 | * | 6/2005 | Watts ............... 602/28 |
| 7,128,725 B2 | * | 10/2006 | Rabe ................ A61F 5/0111 602/23 |
| 2003/0153862 A1 | * | 8/2003 | Watts .................... A61F 5/0111 602/62 |
| 2003/0204157 A1 | | 10/2003 | Cropper |
| 2003/0233062 A1 | * | 12/2003 | McCormick et al. ......... 602/65 |
| 2004/0236261 A1 | | 11/2004 | McCarthy |

FOREIGN PATENT DOCUMENTS

| | | | |
|---|---|---|---|
| GB | 1298930 A | 6/1972 | |
| GB | 128930 | 12/1972 | |
| GB | 2330309 A | 4/1999 | |
| WO | WO 9316665 A1 * | 9/1993 | ............... A61F 5/00 |

OTHER PUBLICATIONS

International Preliminary Report on Patentability corresponding to PCT/GB2005/004685 dated Jun. 13, 2007.
Written Opinion corresponding to PCT/GB2005/004685 dated Jul. 5, 2006.
European Examination Report corresponding to European Application No. 05813543.5-5121 dated Mar. 11, 2009.

* cited by examiner

ANKLE-FOOT ORTHOSIS

CROSS-REFERENCE TO RELATED APPLICATIONS

The present application is a continuation of U.S. patent application Ser. No. 11/792,473, filing date of Mar. 20, 2008, which is a 35 U.S.C. §371 national stage entry of PCT/GB2005/004685, which has an international filing date of Dec. 6, 2005 and claims priority to UK patent application No. GB 0426729.0, filed on Dec. 6, 2004. Each application listed in this paragraph is incorporated herein by reference in their entirety for all purposes.

This invention relates to ankle-foot orthoses.

Orthoses are mechanical devices which impose forces upon a limb of a patient and which can be used for a variety of different purposes. For example, orthoses can be provided for supportive, functional, corrective or protective purposes, or indeed for a combination of these.

Ankle-foot orthoses are typically used to provide protection to the ankle and foot of a patient as well as to provide support against excessive plantarflexion, or "foot-drop" as it is more colloquially known. Foot plantarflexion is a medical condition that results from disease, trauma or congenital abnormality. Patients affected by the condition typically experience difficulty in walking as their feet tend to drop when lifted off the ground, and to avoid stumbling they typically have to lift their foot higher than they would otherwise have to. It is also not atypical for patients to have problems during the swing-through phase of their gait cycle, as a typical sufferer will tend also to exhibit poor, or impaired, dorsiflexion.

The primary function of an ankle-foot orthosis is to provide a resistance to plantarflexion which helps keep the patient's foot in the correct position when the foot is lifted off the ground. As well as this resistive function, a good ankle-foot orthosis should also provide a degree of assistance to dorsiflexion during the swing-through phase of the patient's gait.

A variety of different ankle-foot orthoses have previously been proposed for resisting plantarflexion, and in some cases for additionally assisting dorsiflexion.

One previously proposed device is commonly known in the art as an "under foot" orthosis. As this colloquial name suggests, the orthosis fits under the foot, and in this case outside of a shoe. This particular device cannot be worn without a shoe, and as such the shoe is an integral component of the orthosis. The orthosis comprises a pair of supporting metal rods, one connected to either side of the shoe in the region of the heel by means of a plantarflexion stop that prevents further foot drop. The upper ends of the rods are connected to a supporting band which is secured about the calf of a patient.

Another previously proposed "under foot" orthosis (which must also be used with a shoe) comprises a rigid one-piece plastics moulding composed of integral sole-abutting and calf-abutting regions. The top of the calf-abutting region is provided with a closure mechanism that enables the device to be secured to the calf of a patient, and the sole abutting region acts in conjunction with the shoe to support the foot of the patient.

Another previously proposed device is known colloquially as an "over foot" orthosis, meaning that the orthosis fits over the front (dorsal) aspect of the foot, rather than under it as in the ahovementioned previously proposed devices. This "over foot" orthosis comprises a rigid plastics shell which is worn up against the shin, and which is secured around the calf by means of an appropriate securing band. The orthosis includes a stirrup which fits over the foot in the region of the instep to provide the patient with a resistance to plantarflexion.

All of the aforementioned orthoses provide the patient with a device which is capable of resisting plantarflexion. However, it is also the case that each of them has a number of attendant disadvantages.

To alleviate these problems, we have previously provided (see granted UK Patent No. 2330309) a sock-like structure which is formed of a resiliently flexible material—such as silicone for example. The sock-like structure, by virtue of the inherent resilience of the material from which it is made, provides a resistance to plantarflexion and also stores energy which can subsequently be released to assist dorsiflexion. The orthosis can be coloured to mimic the colour of the patient's skin (and as such is cosmetically pleasing), can comfortably be worn in a normal off-the-shelf shoe, and need not be worn with a shoe in order to provide a beneficial effect.

The part of the sock-like structure which envelops the patient's ankle and lower leg in use includes an opening (to permit the user to put on the device), and in the preferred arrangement the opening is closed (to secure the orthosis in place on the foot of a patient) by means of respective parts of a mechanical hook and loop closure (such as Velcro®) which are embedded in the sock-like structure. Typically, one part of the closure is provided on the outside of the orthosis adjacent one side of the opening and the other part is provided on the inside surface of a tab extending from the other side of the opening, the closure on the tab being attachable to the closure adjacent the one side of the opening to close the opening, and secure the orthosis in place.

Our previous orthosis represented a quantum leap in the field and alleviated most (if not all) of the disadvantages mentioned above (the bulk of which had long been associated with previously proposed devices), and has proved to be extremely commercially successful. Despite this it is still more expensive to manufacture (and hence more expensive for patients to purchase) than we would otherwise like.

One particular problem we have noted in this regard is that it is difficult to embed the respective parts of the Velcro® closure in the silicone sock-like structure, and that once embedded the closures can sometimes come away from the sock-like structure thereby causing the device to fail. These problems tend to lengthen the time taken to make any one device, and to reduce the yield of the production process as a whole. The effect of this is, ultimately, to make the orthoses more expensive to make, and hence more expensive to purchase, than they otherwise would be.

It is an aim of the present invention to provide an orthosis which avoids, or at least alleviates, these problems. In particular, it is an aim of the invention to provide an orthosis which can more easily be manufactured and hence can be manufactured (and ultimately sold) for less.

In pursuit of the above mentioned aims, a presently preferred embodiment of the invention provides an ankle-foot orthosis comprising: a sock-like structure formed of first and second tubular sections set at an angle to one another, wherein the second tubular section is capable of being opened for insertion of the patient's foot and lower leg into respective ones of said first and second tubular sections, the orthosis further comprising a closure member that can be passed round at least part of the periphery of the second tubular section and secured in place to urge the second tubular section towards a closed position in which the second tubular section is closely fitted to the lower leg of the patient.

The principal advantages of this orthosis over that which we previously proposed, is that it can be manufactured more quickly (albeit at the cost of a slight reduction in its aesthetic appearance), and with fewer failures. By reducing the time taken to make any one given orthosis and the number of failed devices, it is possible to significantly increase the yield of the manufacturing process and hence to reduce the manufacturing cost (and ultimately the sale price) of each of the orthoses. In tests we have found that the manufacturing time for an orthosis as described herein can be reduced by approximately 40 percent as compared to the manufacturing time for an orthosis as described in our previous GB patent. This reduction in manufacturing time allows us to sell orthoses of the type described herein for about half the price of orthoses of the type described in our earlier GB patent.

In a highly preferred embodiment, the closure member is located outside of the periphery of the second tubular section when the second tubular section is in the aforementioned closed position.

Further objects, features and advantages of embodiments of the present invention will be apparent from the detailed description that follows.

Various preferred embodiments of the invention will now be described, by way of illustrative example only, with reference to the accompanying drawings, in which.

Figure 1:
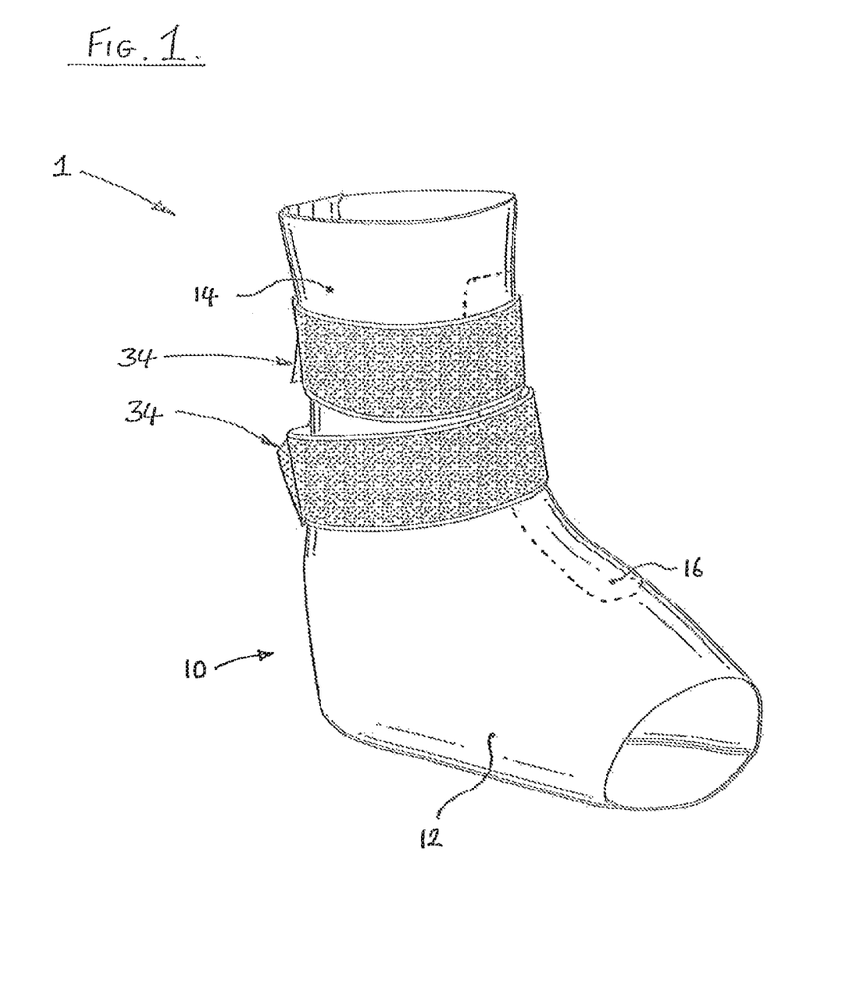
FIG. 1 is a schematic front perspective view of an orthosis in accordance with a preferred embodiment of the present invention in a closed configuration.
Figure 2:
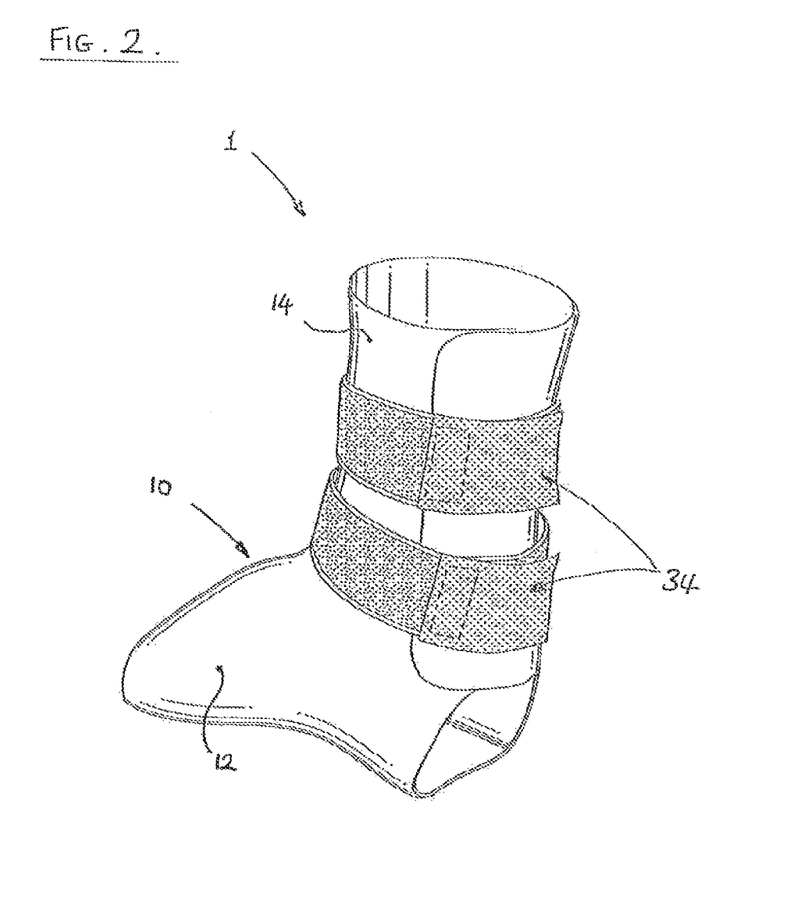
FIG. 2 is a rear perspective view of the orthosis depicted in FIG. 1.
Figure 3:
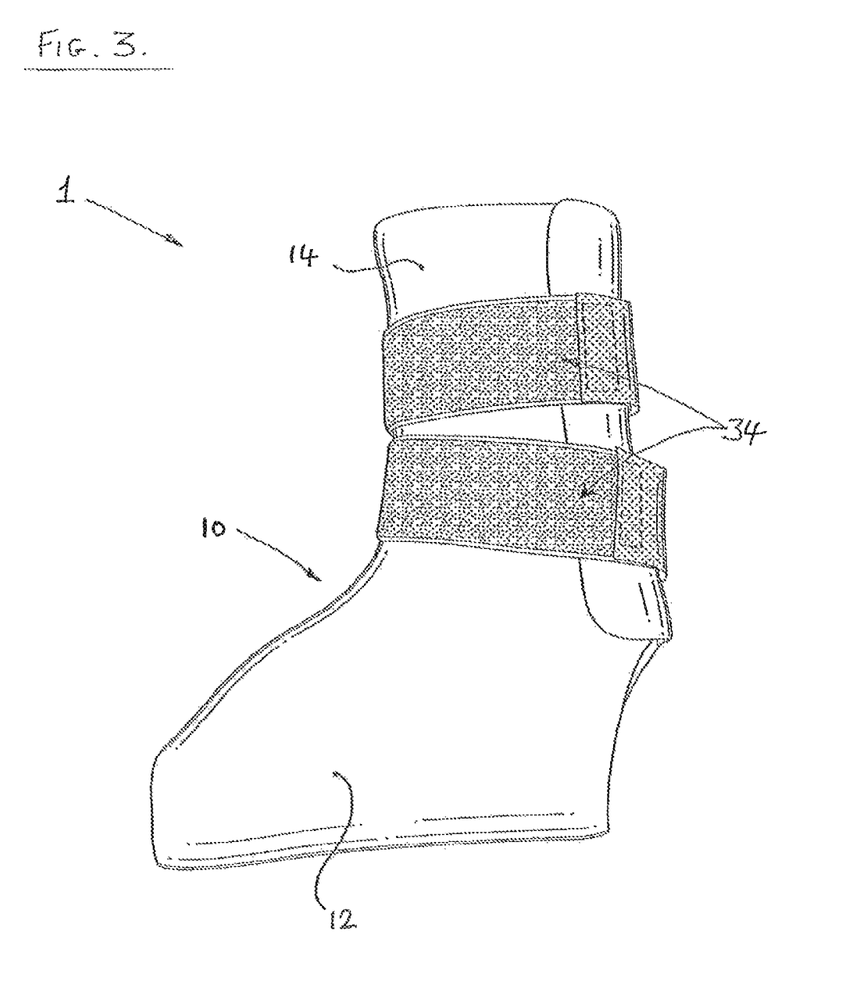
FIG. 3 is a side elevation of the orthosis depicted in FIGS. 1 and 2.

FIG. 1 is a perspective view of an embodiment of the invention in a closed configuration. The orthosis 1 depicted in FIG. 1 is shown as it would appear when worn by a patient (the patient's foot, ankle and lower leg having been omitted for clarity), although it worth noting that the orthosis is sufficiently resilient to keep its three dimensional shape (generally as shown in FIG. 1) when not being worn by the patient.

The orthosis comprises an orthotic structure 10 which is comprised of a first tubular section 12 and a second tubular section 14. The first and second tubular sections are contiguous, and in most instances the second tubular section 14 will have been integrally formed with the first tubular section 12. The first and second tubular portions are set at an angle to one another to provide, at least in use, a generally L-shaped internal cavity 16 (FIG. 4) which is sized such that the orthosis accepts and fits closely about the foot, ankle and lower leg of a patient (not shown) in use.

In a highly preferred arrangement the sock-like structure is formed not so that the first section is set perpendicular to the second, but so that the structure exhibits approximately 3 to 10, preferably 5, degrees of dorsiflexion. This dorsiflexion drops to zero when the orthosis is being worn by a patient and the weight of their foot is applied to the orthosis during the swing through phase of their gait.

The orthotic structure 10 may be described as being generally "sock-like", or in other words akin to a sock, in that when worn by a patient the second section 14 envelops a portion of the patient's lower leg including the medial malleolus (the inside of the ankle) and the lateral malleolus (the outside of the ankle), and the first section 12 envelops at least a portion of the plantar aspect of the foot (the sole of the foot) and at least a portion of the dorsal aspect of the foot (the front of the foot).

In the preferred arrangement (as depicted) the orthotic structure is configured so that the patient's toes and calcaneum (heel) are exposed. This is because we have found that an orthosis which exposes the heel and toes is significantly more comfortable for the patient to wear, whilst also giving the patient a greater sense of confidence when walking (particularly when barefoot) on a given surface due to the fact that their toes and heel can grip that surface. It will be appreciated, however, that the orthosis may instead be configured to envelop the toes and/or heel if desired. As a further alternative for those patients with particularly sensitive ankles, the first and second sections may be configured so that the walls of the first and second sections are thinned or include apertures in those regions of the structure which would normally overlie the medial and lateral malleolae.

The resilience of the orthotic structure 10 is chosen, and may be varied, in dependence upon the degree to which the patient suffers from plantarflexion. In particular, the resilience of the orthotic structure 10 is chosen to provide a resistance to plantarflexion that is sufficient for correcting the particular degree of excessive plantarflexion experienced by the patient who is going to be using the orthosis.

Variations in the resilience of a given orthotic structure 10 (as may be required for patients experiencing a lesser or greater degree of excessive plantarflexion) may be effected by changing the material from which the orthotic structure is formed, by changing the thickness of the orthotic structure, or by incorporating reinforcing means—such as a resilient rib—into the orthosis (or indeed by means of a combination of these).

As an illustrative example, the orthotic structure could include reinforcing means in the form of a resilient rib 16 (shown in ghost in FIG. 1) that extends part-way along the dorsal aspect of the foot. The rib 16 could be formed integrally with the orthosis, or could be removably insertable into a pocket provided on the dorsal aspect of the orthotic structure. The latter arrangement would be particularly useful in that it would allow for the stiffness of the rib and/or the angle of support (by inserting differently shaped ribs) to be changed if desired. The rib may be of the same material as the remainder of the orthotic structure 10, or may be of a different—preferably more resilient—material such as plastics, metal or carbon fibre.

The first 12 and second 14 tubular sections are formed of a resiliently flexible material, and in the preferred embodiment this material is a silicone elastomer. Preferably the silicone elastomer has a Shore A durometer of 30 to 80, preferably of 40 to 70, and most preferably of 50 or 65.

The use of a resilient material for the orthotic structure 10 (and optionally for the rib, if provided) is a fundamental departure from "under foot" or "over foot" devices of the type described above. These previously proposed devices recommended the use of a non-resilient, rigid, material. The primary advantage of using a resilient material as opposed to a rigid material is that the material can flex to store energy during certain phases of the patient's gait, and release that energy during other phases of the patient's gait (in particular the swing-through phase) to thereby actively assist the walking process as a whole, and dorsiflection in particular.

Dorsiflexion and plantarflexion of a foot is predominantly controlled by the tibialis anterior muscle and tendon, and the structure of the orthosis functions to assist the operation of this muscle—in particular for those patients who experience persisting foot drop resulting from a neurological impairment caused, for example, by trauma, disease or genetics. This bio-mechanical function of the device of the invention is fundamentally different to so-called athletic support stockings, for example those of the Tubigrip® type, which provide no means for assisting the operation of the tibialis anterior muscle and tendon (to resist plantarflexion and assist dorsiflexion of a patient's foot), and are instead wholly concerned with resisting abnormal lateral movement of the foot.

As aforementioned, the orthotic structure 10 is closely fitted to the foot and lower leg of the patient and as such may be configured to provide a compressive force to the foot and lower leg of the patient. In a preferred embodiment, the compressive force may be tailored to help treat other conditions such as the effects and symptoms of venous insufficiency, for example varicose veins. It is also conceivable for different regions of the orthotic structure to provide different compressive forces. For example, the orthotic structure may exert a greater compressive force on the foot of the patient than on the ankle in order to provide a pumping effect to assist blood flow to and from the foot.

Figure 4:
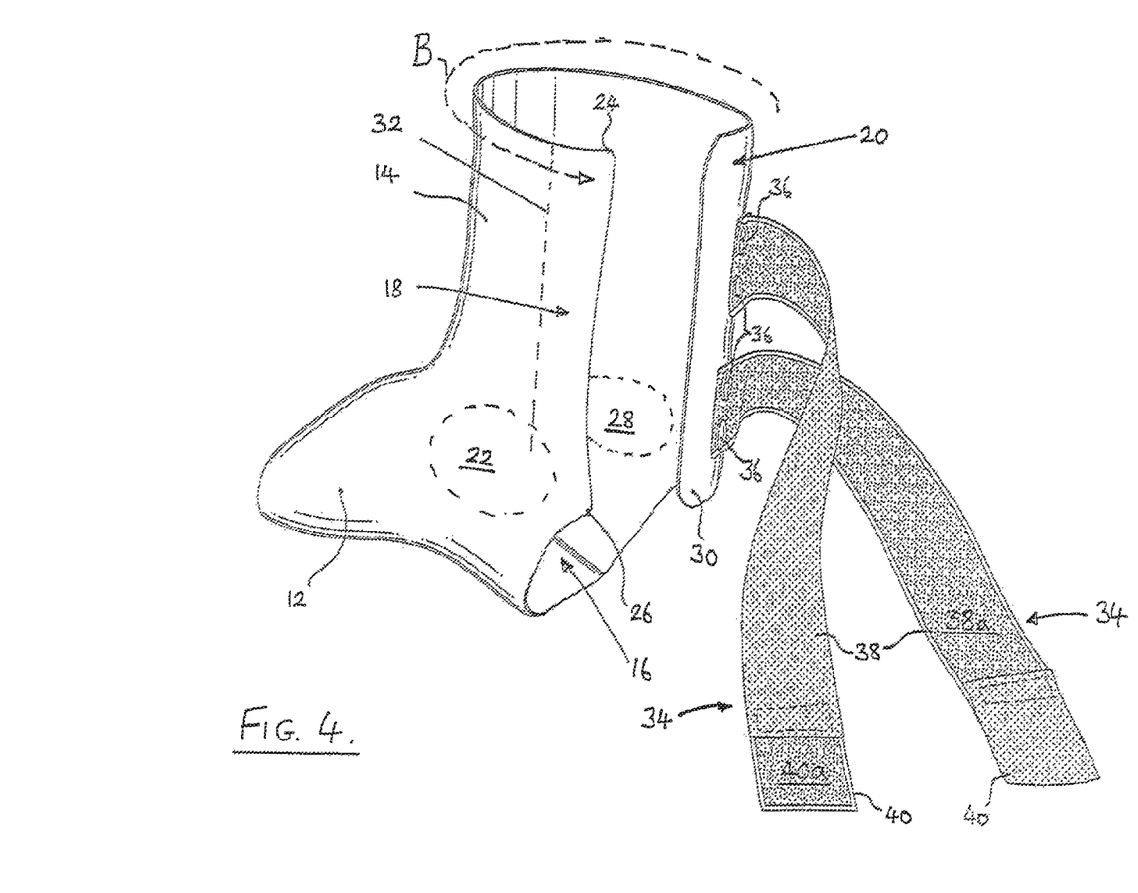
FIG. 4 is a rear perspective view of the orthosis depicted in FIG. 1 in an open configuration.
Figure 5:
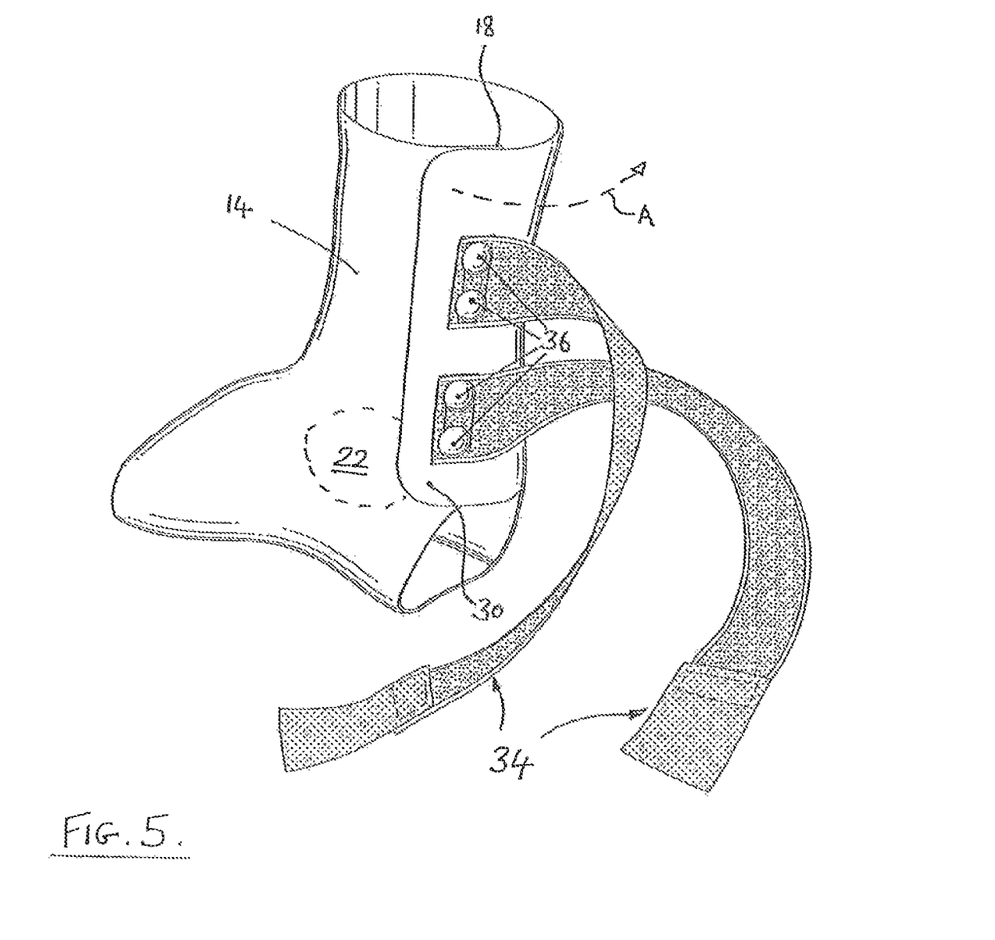
FIG. 5 is a rear perspective view of the orthosis depicted in FIG. 4 in a partly closed configuration.

Referring now to FIGS. 4 & 5, the second tubular section 14 of the orthotic structure is configured so that it can be opened to permit the orthosis to be put on by a patient. In this embodiment opening of the second tubular section 14 is achieved by configuring the second tubular section so that it comprises a second part 20 that is arranged to overlap a first part 18 when the orthosis 1 is in a closed position fitted about the lower leg of the patient—the second part 20 being moveable (in a direction A indicated generally in FIG. 5) away from the first part 18 to open the second tubular section 14.

in the preferred arrangement, as depicted, the first part 18 comprises a part of the second tubular section 14 which extends generally from a part 22 of the orthotic structure 10 which overlies the medial malleolus when the orthosis is worn by a patient, and terminates at a line running longitudinally from an uppermost edge 24 of the second tubular section 14 (i.e. that edge which is in the vicinity of the patient's lower leg in use) to a lowermost edge 26 of the second tubular section 14 (i.e. that edge which is in the vicinity of the patient's calcaneum in use) generally midway between the part 22 of the second tubular section that is arranged to overlie the patient's medial malleolus in use and a part 28 (FIG. 4) of the second tubular section that is arranged to overlie the patient's lateral malleolus in use. The second part 20 comprises a part of the second tubular section 14 which extends generally from the part 28 (FIG. 4) of the orthotic structure 10 which overlies the patient's lateral malleolus to form a tab portion 30 which overlaps the first part 18 when the second tubular section 14 is closed. In the preferred arrangement the tab portion 30 overlaps the first part 18 (when the second tubular section 14 is closed) to an extent whereby the tab portion 30 terminates at an axial line 32 running longitudinally down the second tubular section and terminating at or about that portion 22 of the orthosis which overlies the patient's medial malleolus in use.

As depicted in FIGS. 4 & 5, in the preferred embodiment the orthosis includes closure members 34 which are fixedly attached to the aforementioned tab portion 30 and which can be used—in a manner described in detail below—to secure the second tubular portion 14 in the aforementioned closed position about the lower leg of the patient. In the preferred arrangement two closure members are provided, but it will be appreciated that a single closure member or more than two closure members may be provided if desired.

In the preferred embodiment, the closure members are fixedly attached to the tab portion by means of tubular double-headed rivets 36, also known as "speed rivets", (or equivalent fixings) the like of which are available from Evans and Evans (Unit 24, Red Lion Business Park, Red Lion Road, Tolworth, Surbiton, Surrey, UK), or Algeos (Sheridan House, Bridge Industrial Estate, Speke Hall Road, Liverpool, L249HB United Kingdom). Whilst it is undoubtedly the case that a variety of different fixings will be immediately evident to those persons skilled in the art, speed rivets are nevertheless preferred as they permit the closure member attachment stage of the orthosis production process to be accomplished more quickly than if the closure members were, for example, to be sown onto the tubular section.

In the preferred embodiment where the tab portion 30 of the second tubular section 14 overlaps the first part 18 it is preferred that the closure members 34 are attached to the tab portion 30 in such a manner that the fixings 36 also overlap the aforementioned first part 18 of the second tubular section 14. This is highly advantageous as it means that the fixings do not bear on the patient's lower leg (where they could cause discomfort) but instead bear upon the first part of the second tubular section.

In the preferred arrangement, the closure members comprise a first strip of material 38 carrying on the outside 38a thereof (i.e. the side facing away from the second tubular section) one part of a mechanical hook and loop securing system (such as Velcro®). A second strip of material 40 carrying on the inside 40a thereof (i.e. the side facing towards the second tubular section) the other part of the mechanical hook and loop securing system is attached (for example sown onto) the free end of the first strip of material 38. In a highly preferred arrangement the first strip of material 38 carries a set of hoops (and the second strip 40 carries the hooks) so that the closure members do not interfere with any clothes that the patient might be wearing.

As mentioned above, the closure members are provided to enable the second tubular section to be secured in the aforementioned closed position. To this end, the closure members can be wound (in the direction B indicated in FIG. 4—i.e. in a continuation of the direction A (FIG. 5) in which the tab portion 30 may be moved to open the second tubular section 14) round the periphery of the second tubular section 14 until the hooks or loops on the second strip of material 40 overlie the loops or hooks on the first strip of material 38, whereupon the second strip of material 40 can be secured to the first 38 to secure the second tubular section 14 in the closed position.

As an alternative, the closure members 34 could be affixed to the tab section 30 in such a way that they are wound in the opposite direction (i.e. in a direction which would move the tab portion to close the second tubular portion) and then secured as aforementioned. However, such an arrangement is less preferred as pulling the closure member(s) in a direction which acts to close the tubular section 14 may encourage the patient to overtighten the second tubular section about their lower leg, perhaps to a point where the second tubular section is secured so tightly that it impacts adversely on the circulation in the patients lower leg and foot. This is particularly the case for those patients who have suffered nerve damage and might not immediately be aware that the orthosis has been overtightened.

Figure 6:
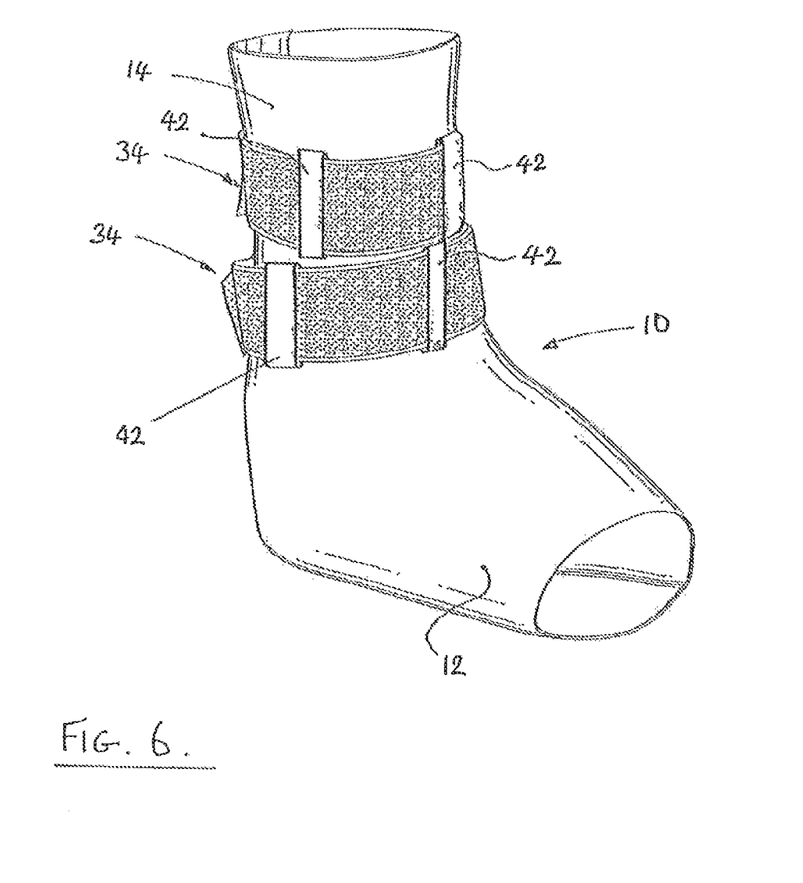
FIG. 6 is a schematic front perspective view of an orthosis in accordance with a second embodiment of the invention.

Whilst the above arrangement is preferred, it will be apparent that a number of other alternatives are possible. For example, it is not necessary for the closure members to be attached to the second tubular section. The closure members could be detachable from the second tubular member, and simply secured around it. The second tubular section 14, as depicted schematically in FIG. 6, could also be provided with a number of hoops 42 through which fully detachable closure members 34 could be threaded and secured (as depicted).

Figure 7:
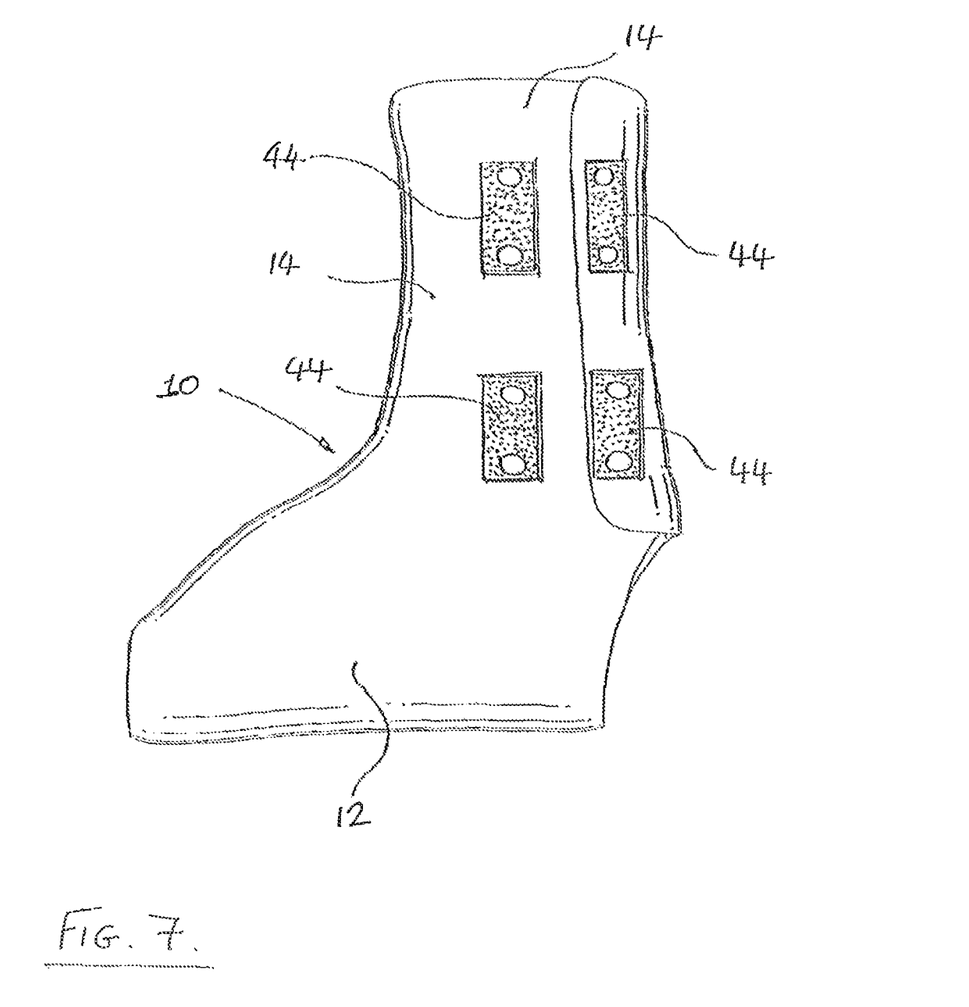
FIG. 7 is a schematic side view of an orthosis in accordance with a third embodiment of the invention.

As a further alternative, depicted schematically in FIG. 7, the closure member could comprise a strip of material (not shown) that is fully detachable from the orthosis and which carries hooks or loops of a mechanical hook and loop engagement mechanism. The orthosis has two strips of material 44 per closure member fixedly attached (for example by means of speed rivets 46 or equivalent fixings) to the second tubular section 14—the first being attached to the outside of the aforementioned tab portion and the second being attached to the outside of a region of the aforementioned first part of the second tubular section which is not overlapped by the tab portion when the second tubular section is closed. Each of the strips of material carry loops or hooks of the mechanical hook and loop engagement mechanism, so that the detachable strip of material can be secured to each of the two attached strips of material to hold the second tubular section in the closed position.

Figure 8:
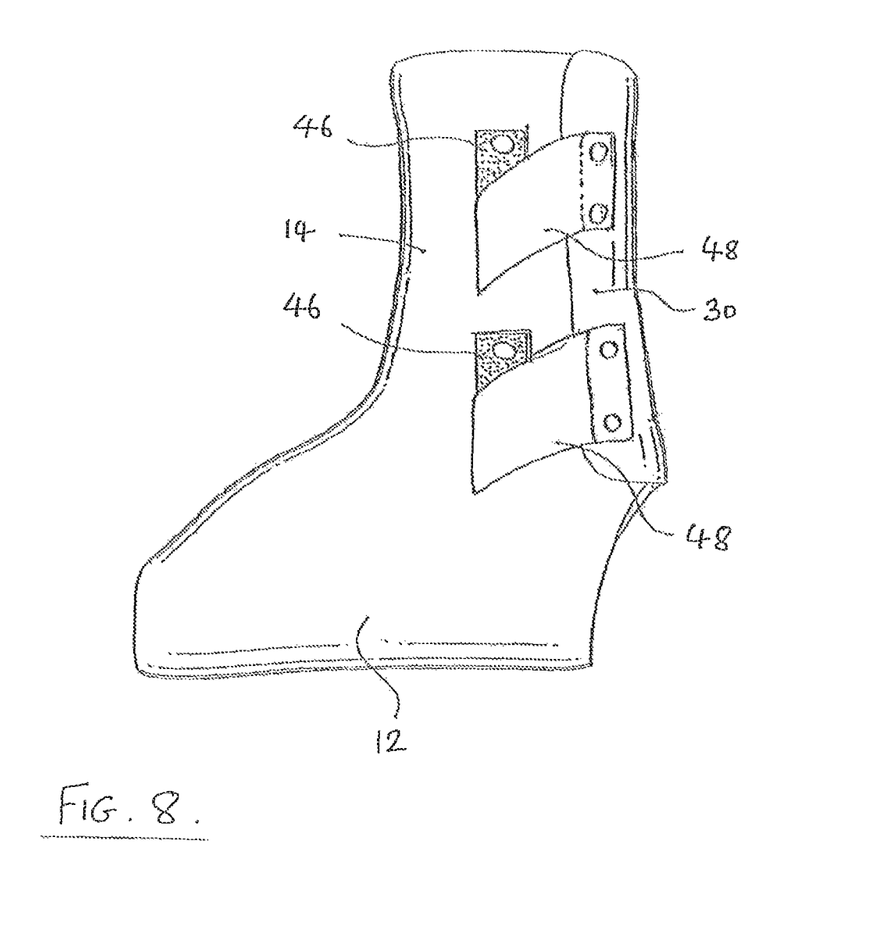
FIG. 8 is a schematic side view of an orthosis in accordance with a fourth embodiment of the invention.

As a yet further alternative depicted schematically in a partly closed position in FIG. 8, a strip of material 46 (carrying hooks or loops of a mechanical hook and loop engagement mechanism on its outwardly face) may be attached to the outside of a region of the second tubular section 14 which is not overlapped by the tab portion 30 when the second tubular section 14 is closed A second strip 48 of material, fixedly attached at one end to the tab portion 30 and carrying on its underside (i.e. the side facing the second tubular section) loops or hooks of the mechanical engagement mechanism may then be secured to the strip of material 46 fixedly attached to the second tubular section to secure the second tubular section in the aforementioned closed position.

In another modification of the preferred embodiment depicted in FIGS. 4 & 5, the closure member 34 does not necessarily need to comprise two strips of material (38, 40) attached to one another. Rather, the closure member could instead comprise a single strip of material provided with hooks or loops of the mechanical engagement mechanism on one side, and loops or hooks of the mechanism provided on the other. As a further modification, the mechanical hook and loop closure mechanism could be replaced by another type of fixing—such as press studs for example.

In a further alternative arrangement, not depicted in the drawings, the second tubular portion could be longitudinally split, with respective edges of the split being joined by a section of elastic material—the elastic material being sown or otherwise affixed to the resilient material of the second tubular portion, and permitting the second tubular section 14 to be opened for the insertion of a patient's foot and lower leg. Any of the abovementioned closure members could then be provided to secure the second tubular section around the patient's lower leg (suitable modifications being made to account for the absence of a tab portion).

As a further alternative arrangement it will be apparent to those persons skilled in the art that the tab portion 30 of the second tubular portion 14 need not overlap the first part 18. The second tubular portion 14 could simply comprise a longitudinal slit, one or more closure members being provided to bring opposed edges of the slit towards one another to close the slit and secure the second tubular section about the lower leg of the patient. Such an arrangement, whilst eminently possible, is less preferred as the fixings used to attach the closure member(s) to the orthosis would then be in contact with the patient's lower leg.

Yet further configurations which permit the second tubular section to be opened will be apparent to those persons skilled in the art, but it remains the case that the configuration described in detail above with reference to FIGS. 1 to 5 is most preferred as the resulting orthosis can more quickly be manufactured than an orthosis which included a strip of elastic material, for example.

As mentioned above, one advantage of the orthosis described herein is that it can be manufactured much more quickly than the orthosis described in our prior GB patent. Fabrication of an orthosis in accordance with that prior patent necessitated the encapsulation of Velcro® strips in the material of the orthosis to provide a means for closing the insertion slit in the second tubular section. To manufacture an orthosis in accordance with the teachings provided herein all one need do is fixedly attach the closure member(s) to the second tubular section for example by means of speed rivets, a much faster and much more robust alternative to the encapsulation of strips of Velcro® in the body of the orthosis. The orthotic structure of either embodiment may be coloured so that it can be matched to the skin colour of the patient (as can the closure member(s)), and may be provided in a variety of different sizes and shapes. The orthotic structure may be manufactured by injection moulding but may alternatively be manufactured by milling (as described below) and subsequently building up layers of silicone elastomer upon a suitable cast (typically of a patient's foot and lower leg).

The orthotic structure, as mentioned above, may be manufactured from a number of different resiliently flexible materials. Amongst these, silicone elastomer is a particularly preferred material. Two suitable elastomers are sold under the product names HCR9960 and MED4035 by Nusil Technology of 1050 Cindy Lane, Carpinteria, Calif., USA. Another family of suitable elastomers are sold by Nusil Technology under the registered trademark VersaSil3®.

HCR9960 has a working time of approximately 1:2 hours and MED4035 has a shorter working time of approximately 3 to 4 hours, after which the elastomer cures. The elastomers are thermosetting and are strained through a 200 mesh screen to remove particulate contaminants.

The elastomers are supplied as A and B components which are preferably combined in equal portions on a two roll mill, or other suitable device, prior to use.

A suggested sequence for blending the two components is to first soften part B on the mill and then soften part A, after which an equal weight of part B should be added to part A and then thoroughly mixed. At this stage, it is recommended to keep the temperature of the material as low as possible so as to maximise the table life of the elastomer. The mixture may then be manually fitted to a plaster cast of a patient's foot, or more preferably supplied to injection moulding apparatus to mould a suitably shaped orthotic. Curing of the blended elastomer may be accelerated by heat and can take from 3 to 4 hours. The cure may be inhibited by any ambient traces of organic rubbers and other substances and thus it is important for the fabrication of the orthotic structure to be conducted in a thoroughly cleaned area.

The VersaSil3® family of elastomers include 3 base stocks which when vulcanised produce tough, durable elastomers with Shore A durometers of 30, 50 and 70, and the base stocks can be blended to produce elastomers of intermediate durometer. The three base stocks are compounded with CAT-40 and CAT-55—CAT 40 being an inhibitor, and CAT-55 being a platinum catalyst.

Each series (i.e. 30, 50 or 70 durometer) is supplied as a three part system which must be compounded, for example on a two roll mill, prior to use. Elastomers of intermediate durometer can be produced by blending 30, 50 or 70 durometer elastomers in a 1:1 ratio. For example, a 40 durometer elastomer can be achieved by blending VersaSil3® 30 and VersaSil3® 50 in a 1:1 ratio mix.

To produce a given elastomer it is suggested to soften approximately 25% of the total required base stock on a cooled two roll mill. The entire required quantity of CAT-40 should then be added, and the resulting mixture milled until homogeneous. Whilst the base/CAT-40 mixture is turning on the mill, small increments of CAT-55 should be added until the entire required amount has been added. Next the remaining base stock should added and milled. Once the elastomer has been produced, the mixture may then be manually fitted to a plaster cast of a patient's foot or more preferably supplied to injection moulding apparatus to mould a suitably shaped orthotic structure.

Cure of the resulting mixture is accelerated by heat. For example, the elastomer will cure in a mould cross-section up to 0.075 inch (0.00195 m) thick in less than ten minutes at 116° C. The vulcanisation rate can be increased by increasing the cure temperature, and an optional post cure, such as four hours at 177° C. may be implemented if desired. An important point to note is that cure of the elastomer may be inhibited by traces of amines, sulphur, nitrogen oxide, organo-tin compounds and carbon monoxide. As such it is important for manufacture of the orthotic structure to be conducted in a thoroughly clean environment.

The performance of the device described herein is expected to be at least on a par with that provided by our previously proposed device (as described in granted UK. Patent No. 2330309). This device was found to provide a considerable improvement not only to the degree of plantarflexion, but also to the walking speed and the effort involved in walking (known as the Physiological Cost index or PCI) of a group of patients. At an initial point in the study it was found that the orthosis provided an increase of roughly 10% in walking speed and a reduction of roughly 2% in the PCI. At the end of the study, roughly six months later, it was found that that same group of patients experienced an increase in walking speed of roughly 20% and a reduction of roughly 32% in the PCI as compared to when they were initially without the orthosis. It is anticipated that the orthosis of the present invention will provide similar, and hopefully, better results.

We have also found that the orthosis of the present invention improves the patient's proprioception. When not wearing an orthosis as herein described, patients tend to stumble when walking. However, when the orthosis is worn, the pressure exerted by the orthosis on the skin receptors sends a message to the brain that helps the patient determine where the foot is in space. This in turn helps the patients to walk faster and avoid stumbling.

It will be understood from the above that the orthoses herein described provide an effective means to tackle the problem of plantarflexion. Advantageously, and in addition to this function, the orthoses herein described can significantly augment dorsiflexion during the swing through phase of a patient's gait cycle. The principal reason for this is believed to be that the orthotic structure (and resilient rib, if provided) store energy when compressed, and this energy is released during the swing through phase of the patient's gait cycle. It is anticipated, therefore, that patients will not only find that the orthoses of the embodiments tackle the problem of plantarflexion but also actively assist the walking process.

Whilst various preferred embodiments have been described above in detail, it will be apparent and should be noted that modifications and alterations may be made without departing from the spirit and scope of the invention as defined by the accompanying claims. It should also be noted that whilst particular combinations and permutations of features have been explicitly enumerated in the accompanying claims, the scope of the invention is not limited to those combinations and instead extends to encompass any combination of features herein described irrespective of whether that particular combination of features has explicitly been claimed.

The invention claimed is:

1. An ankle-foot orthosis for resisting plantarflexion of a patient's foot, comprising:
    a resiliently flexible sock-like orthotic structure integrally formed as a single piece and having first and second tubular sections set at a non-perpendicular angle relative to one each other to provide about 3 to 10 degrees of dorsiflexion when not being worn, wherein:
    the orthotic structure is sufficiently resilient to maintain a three-dimensional shape when not being worn;
    the second tubular section comprises first and second edge portions, the second edge portion being separable from the first portion to permit the second tubular section to be opened for insertion of the patient's foot and lower leg into respective ones of the first and second tubular sections, the second edge portion being configured to overlie the first edge portion when the second tubular section is in a closed position;
    the first edge portion is configured to extend from a portion of the orthosis that overlays a medial malleolus portion of the patient's foot when the orthosis is worn by the patient and the first edge portion terminates at a line running longitudinally from an uppermost edge of the second tubular portion;
    the second edge portion is configured to extend generally from a portion of the orthosis that overlays a lateral malleolus portion of the patient's foot when the orthosis is worn by the patient.

2. The orthosis according to claim 1, further comprising at least one closure member wherein the at least one closure member is located outside of a periphery of the second tubular section when the second tubular section is in the closed position.

3. The orthosis according to claim 2, wherein the second tubular section is longitudinally split to define an insertion slit, and first and second edge portions of the slit, which define the first and second edge portions of the second tubular section, are configured to lie substantially adjacent one another when the second tubular section is in the closed position.

4. The orthosis according to claim 3, wherein the at least one closure member is fixedly attached to the orthotic structure.

5. The orthosis according to claim 4, wherein the at least one closure member comprises a first closure fixedly attached to said second tubular section, and a second closure fixedly attached to the second edge portion, at least a free end of the second closure being securable to the first closure to secure the second tubular portion in said closed portion.

6. The orthosis according to claim 5, wherein said first closure and at least part of said second closure include appropriate complimentary parts of a mechanical hook and loop securing system to permit the second closure to be secured to said first closure.

7. The orthosis according to claim 4, wherein the at least one closure member comprises a strap fixedly attached at one end to one of said first and second edge portions, said strap being configured to be passed round the entire circumference of the second tubular section before being secured to itself to urge the second tubular section towards the closed position.

8. The orthosis according to claim 7, wherein at least parts of respective faces of said strap include appropriate complimentary parts of a mechanical hook and loop securing system to permit the strap to be secured to itself once it has been passed round the entire circumference of the second tubular section.

9. The orthosis according to claim 8, wherein the closure member comprises a strap fixedly attached by means of speed rivets to said second edge portion, such that the speed rivets bear on said first edge portion when the orthosis is in the closed position and not on the patient's lower leg.

10. The orthosis according to claim 3, wherein the at least one closure member is partly separable from the orthotic structure.

11. The orthosis according to claim 2, wherein each said at least one closure member comprises first and second closures fixedly attached to the second edge portion, and a removable closure strip attachable to both of said first and second closures to secure the second tubular section in said closed position.

12. The orthosis according to claim 11, wherein said first and second closures are fixedly attached by means of one or more speed rivets.

13. The orthosis according to claim 11, wherein said first and second closures and said removable closure strip include appropriate parts of a mechanical hook and loop securing system to permit the strip to be secured to each of the first and second closures.

14. The orthosis according to claim 2, wherein the at least one closure member comprises a first closure fixedly attached to said second tubular section, a second closure fixedly attached to the second edge portion, and a removable closure strip attachable to both of said first and second closures to secure the second tubular section in said closed position.

15. The orthosis according to claim 2, wherein said at least one closure member is wholly removable from the orthotic structure and is configured to be passed round the entire circumference of the second tubular section before being secured to itself to urge the second tubular section towards the closed position.

16. The orthosis according to claim 15, wherein said second tubular section carries a plurality of loops through which a said closure member can be threaded to retain the closure member in a fixed position with respect to the second tubular section.

17. The orthosis according to claim 15, wherein respective faces of said closure member include appropriate parts of a mechanical hook and loop securing system to permit the closure member to be secured to itself once it has been paused round the entire circumference of the second tubular section.

18. An ankle-foot orthosis for resisting plantarflexion of a patient's foot, comprising:
a resiliently flexible sock-like orthotic structure integrally formed as a single piece, the orthotic structure being sufficiently resilient to maintain a three-dimensional shape when not being worn, the orthotic structure comprising:
a first tubular section;
a second tubular section arranged at a non-perpendicular angle relative to the first tubular section to provide about 3 to 10 degrees of dorsiflexion when not being worn, and comprising:
a first edge portion;
a second edge portion, the second edge portion being separable from the first edge portion to permit the second tubular section to be opened for insertion of the patient's foot and lower leg into respective ones of the first and second tubular sections, the second edge portion being configured to overlie the first edge portion when the second tubular section is in a closed position;
wherein the first edge portion is configured to extend from a portion of the orthosis which overlays a medial malleolus portion of the patient's foot when the orthosis is worn by the patient and the first edge portion terminates at a line running longitudinally from an uppermost edge of the second tubular portion;
wherein the second edge portion is configured to extend from a portion of the orthosis that overlays a lateral malleolus portion of the patient's foot when the orthosis is worn by the patient.

19. The orthosis of claim 18, further comprising at least one closure member, wherein the at least one closure member is located outside of a periphery of the second tubular section when the second tubular section is in the closed position.

20. The orthosis according to claim 19, wherein the second tubular section is longitudinally split to define an insertion slit, first and second edge portions of the slit being configured to lie substantially adjacent one another when the second tubular section is in the closed position.

* * * * *